United States Patent
Fukushima et al.

(10) Patent No.: US 9,758,456 B2
(45) Date of Patent: Sep. 12, 2017

(54) METHOD FOR STORING TETRAFLUOROPROPENE AND CONTAINER FOR STORING TETRAFLUOROPROPENE

(71) Applicant: ASAHI GLASS COMPANY, LIMITED, Tokyo (JP)

(72) Inventors: Masato Fukushima, Tokyo (JP); Masaaki Tsuzaki, Tokyo (JP); Maki Shigematsu, Tokyo (JP)

(73) Assignee: Asahi Glass Company, Limited, Tokyo (JP)

(*) Notice: Subject to any disclaimer, the term of this patent is extended or adjusted under 35 U.S.C. 154(b) by 1 day.

(21) Appl. No.: 15/185,584

(22) Filed: Jun. 17, 2016

(65) Prior Publication Data

US 2016/0289148 A1    Oct. 6, 2016

Related U.S. Application Data

(60) Division of application No. 14/524,629, filed on Oct. 27, 2014, now Pat. No. 9,428,430, which is a continuation of application No. PCT/JP2013/061678, filed on Apr. 19, 2013.

(30) Foreign Application Priority Data

Apr. 27, 2012 (JP) ................. 2012-103184

(51) Int. Cl.
| | |
|---|---|
| F17C 5/00 | (2006.01) |
| F17C 5/02 | (2006.01) |
| F17C 5/04 | (2006.01) |
| F17C 5/06 | (2006.01) |
| C07C 21/18 | (2006.01) |
| C07C 17/38 | (2006.01) |
| C07C 21/185 | (2006.01) |

(52) U.S. Cl.
CPC ............... *C07C 21/18* (2013.01); *C07C 17/38* (2013.01); *C07C 21/185* (2013.01); *F17C 5/00* (2013.01)

(58) Field of Classification Search
CPC ......... F17C 5/00; F17C 5/02; F17C 5/04; F17C 5/06

See application file for complete search history.

(56) References Cited

U.S. PATENT DOCUMENTS

| | | | |
|---|---|---|---|
| 2011/0079040 A1 | 4/2011 | Morimoto et al. | |
| 2011/0312101 A1 | 12/2011 | Tsuchiya et al. | |
| 2012/0204586 A1 | 8/2012 | Kawabe et al. | |

FOREIGN PATENT DOCUMENTS

| | | |
|---|---|---|
| JP | 2008-308480 | 12/2008 |
| JP | 2011-16930 | 1/2011 |
| JP | 2011-85275 | 4/2011 |
| JP | 2011-85360 | 4/2011 |
| JP | 2011-226728 | 11/2011 |
| WO | 2009/157325 | 12/2009 |
| WO | 2010/098447 | 9/2010 |
| WO | 2010/098451 | 9/2010 |

OTHER PUBLICATIONS

Third Party Observation mailed Aug. 26, 2014, in PCT/JP2013/061678 filed Apr. 19, 2013, with attached reference (2011 Standard for Specifications for Fluorocarbon Refrigerants).
International Search Report issued Jul. 30, 2013 in PCT/JP2013/061678 filed Apr. 19, 2013.

*Primary Examiner* — Medhanit Bahta
(74) *Attorney, Agent, or Firm* — Oblon, McClelland, Maier & Neustadt, L.L.P.

(57) ABSTRACT

To provide a method for stably storing tetrafluoropropene filled in a container for e.g. storage or transportation, without occurrence of reaction such as polymerization.

A method for storing tetrafluoropropene in a gaseous-liquid state composed of a gas phase and a liquid phase in a closed container, wherein the oxygen concentration (content) in the above gas phase is adjusted to at least 3 vol ppm and less than 3,000 vol ppm at a temperature of 25° C.

3 Claims, No Drawings

METHOD FOR STORING TETRAFLUOROPROPENE AND CONTAINER FOR STORING TETRAFLUOROPROPENE

CROSS REFERENCE TO RELATED APPLICATIONS

The present application is a divisional of U.S. patent application Ser. No. 14/524,629, filed on Oct. 27, 2014, the text of which is incorporated herein by reference and which is a 35 U.S.C. §371 national stage patent application of international patent application PCT/JP2013/061678, filed on Apr. 19, 2013, the text of which is incorporated herein by reference and which claims priority to Japanese patent applications JP 2012-103184, filed on Apr. 27, 2012, the text of which is incorporated herein by reference.

This application is a continuation of PCT Application No. PCT/JP2013/061678 filed on Apr. 19, 2013, which is based upon and claims the benefit of priority from Japanese Patent Application No. 2012-103184 filed on Apr. 27, 2012. The contents of those applications are incorporated herein by reference in their entireties.

TECHNICAL FIELD

The present invention relates to a method for storing tetrafluoropropene and a container for storing the same, particularly to a method for stably storing tetrafluoropropene for e.g. storage or transportation and a container for stably storing tetrafluoropropene.

BACKGROUND ART

In recent years, 2,3,3,3-tetrafluoropropene (which is represented by $CF_3CF=CH_2$, hereinafter referred to also as HFO-1234yf) as one of isomers of tetrafluoropropene, has attracted attention as a new refrigerant to replace a chlorofluorocarbon (CFC), a hydrochlorofluorocarbon (HCFC) and a hydrofluorocarbon (HFC) which are greenhouse gases that deplete the ozone layer.

Such HFO-1234yf is stored and transported as filled in a closed container under pressure at ordinary temperature or lower, or as liquefied and filled under pressure under cooling. HFO-1234yf filled in a closed container as such is in a gaseous-liquid state composed of a gas phase and a liquid phase. Further, the HFO-1234yf in a gaseous-liquid state has been required to be stably stored without undergoing reaction such as polymerization, for maintaining quality as a refrigerant or preventing adhesion of impurities (solids) in the container.

It has been known that fluoroolefins undergo polymerization reaction in the presence of oxygen which functions as a radical source. Among fluoroolefins, tetrafluoroethylene is polymerized in the presence of oxygen in a very small amount of from one to a few ten ppm, and in some cases, such a polymerization reaction proceeds explosively. For example, Patent Document 1 discloses that tetrafluoroethylene undergoes polymerization at an oxygen content of 1.4 ppm to form polytetrafluoroethylene. Accordingly, in a case where a fluoroolefin is stored, it is important to reduce oxygen to the utmost limit before treating the fluoroolefin.

However, in order to reduce oxygen to the utmost limit, it is necessary to take new measures such as a step of reducing oxygen to the utmost limit in the production process, and this results in cost increase. Further, if the step of reducing oxygen to the utmost limit is carried out, a yield also tends to be low, and this results in production cost increase.

It remains unknown what extent tetrafluoropropene such as HFO-1234yf is stable to the self-polymerization reaction in the presence of oxygen. In order to maintain the quality as a refrigerant and to carry out storage and transportation safely and stably at a low cost, a method of storing tetrafluoropropene such as HFO-1234yf without occurrence of polymerization reaction has been required.

Heretofore, several proposals for stabilizing hydrofluoropropene have been made. Patent Document 2 proposes a method of adding a stabilizer such as an alkylcatechol or an alkoxyphenol so that hydrofluoropropene is maintained in a stable state (a state where no acid is formed) even in coexistence of air. Further, Patent Document 3 proposes a method of stabilizing hydrofluoropropene by adding a $C_{1-4}$ aliphatic alcohol as a stabilizer to the hydrofluoropropene.

However, both of the methods of Patent Document 2 and Patent Document 3 are based on the premise of the presence of a refrigerating machine oil, they are a method of stabilizing an entire cooling system by stabilizing a refrigerant composition, and their conditions are different from the stabilization of a refrigerant in a container for storage or transportation, and therefore it is difficult to apply these methods to a method of storing a refrigerant in a container. Further, in the method of adding a stabilizer, it is necessary to remove the stabilizer before use of a refrigerant, and therefore not only loads of a step increases, but also there is a case where the stabilizer is not completely removed in a physical purification method such as distillation, such being undesirable in view of quality control.

PRIOR ART DOCUMENTS

Patent Documents

Patent Document 1: JP-A-2008-308480
Patent Document 2: WO2010/098451
Patent Document 3: WO2010/098447

DISCLOSURE OF INVENTION

Technical Problem

Under these circumstances, the object of the present invention is to provide a method for inexpensively and stably storing tetrafluoropropene filled in a container for storage or transportation, without occurrence of reaction such as polymerization, and a container for stably storing tetrafluoropropene.

Solution to Problem

The method for storing tetrafluoropropene of the present invention is a method for storing tetrafluoropropene in a gaseous-liquid state composed of a gas phase and a liquid phase in a closed container, wherein the oxygen concentration in the above gas phase is adjusted to at least 3 vol ppm and less than 3,000 vol ppm at a temperature of 25° C.

In the method for storing tetrafluoropropene of the present invention, it is preferred that the oxygen concentration in the above gas phase is adjusted to at least 5 vol ppm and less than 1,000 vol ppm at a temperature of 25° C. Further, it is preferred that the above tetrafluoropropene is HFO-1234yf.

The container for storing tetrafluoropropene of the present invention is a container for storing tetrafluoropropene, which is filled with tetrafluoropropene in a gaseous-liquid state composed of a gas phase and a liquid phase, and closed, wherein the oxygen concentration in the above gas phase is at least 3 vol ppm and less than 3,000 vol ppm at a temperature of 25° C.

In the container for storing tetrafluoropropene of the present invention, it is preferred that the oxygen concentration in the above gas phase is at least 5 vol ppm and less than 1,000 vol ppm at a temperature of 25° C. Further, it is preferred that the above tetrafluoropropene is HFO-1234yf.

Advantageous Effect of Invention

According to the method for storing tetrafluoropropene and the container for storing tetrafluoropropene of the present invention, it is possible to suppress e.g. polymerization reaction of tetrafluoropropene, and therefore it is possible to maintain tetrafluoropropene with high purity and high quality. Further, since no polymerization product in a solid form is produced in a container, there is no fear of clogging of e.g. a supply valve or contamination into a refrigerant apparatus. Moreover, according to the method for storing tetrafluoropropene and the container for storing tetrafluoropropene of the present invention, it is possible to store it at a low cost.

DESCRIPTION OF EMBODIMENTS

Now, embodiments of the present invention will be described.

According to a first embodiment of the present invention, provided is a method for storing tetrafluoropropene in a gaseous-liquid state composed of a gas phase and a liquid phase under pressure in a closed container, wherein the oxygen concentration in the gas phase is kept to be at least 3 vol ppm and less than 3,000 vol ppm at a temperature of 25° C. Here, since tetrafluoropropene is maintained in a gaseous-liquid state in the closed container, tetrafluoropropene has a saturated vapor pressure in a gas phase. The above oxygen concentration may be considered as a content showing to what extent oxygen is contained in the gas phase of tetrafluoropropene.

The container for storing tetrafluoropropene according to a second embodiment of the present invention is one filled with tetrafluoropropene in a gaseous-liquid state in a closed container, in which the oxygen concentration in the gas phase is kept to be at least 3 vol ppm and less than 3,000 vol ppm at a temperature of 25° C.

In such first and second embodiments of the present invention, tetrafluoropropene may, for example, be trans-1,3,3,3-tetrafluoropropene (E-HFO-1234ze), cis-1,3,3,3-tetrafluoropropene (Z-HFO-1234ze), trans-1,2,3,3-tetrafluoropropene (E-HFO-1234ye), cis-1,2,3,3-tetrafluoropropene (Z-HFO-1234ye), 1,1,3,3-tetrafluoropropene (HFO-1234zc), 1,1,2,3-tetrafluoropropene (HFO-1234yc) or 2,3,3,3-tetrafluoropropene (HFO-1234yf). Especially, preferred is 2,3,3,3-tetrafluoropropene (HFO-1234yf) which has attracted attention as a new refrigerant in recent years.

The container for storing tetrafluoropropene is not required to have a specific structure or constituting material so long as it is a closed container capable of sealing a gaseous liquid mixture under internal pressure, and it may have wide ranges of embodiments and functions. For example, a pressure-resistant container such as a storage tank as a storage container fixed, a filling cylinder used for transportation or a secondary filling cylinder (refrigerant can) may be mentioned. Further, as the constituting material for a storage container, for example, a carbon steel, a manganese steel, a chromium-molybdenum steel or other low-alloy steels, a stainless steel or an aluminum alloy may be used.

The oxygen concentration in the gas phase is at least 3 vol ppm and less than 3,000 vol ppm at 25° C. When the oxygen concentration in the gas phase is less than 3,000 vol ppm, it is possible to sufficiently prevent reaction such as polymerization of tetrafluoropropene in a liquid phase and a gas phase. Further, the present inventors have conducted extensive studied on the relation between the oxygen concentration of tetrafluoropropene and the progress of polymerization, and as a result, have found that no polymerization of tetrafluoropropene proceeds if the oxygen concentration in the gas phase of tetrafluoropropene is from 0 to 3 vol ppm. On the basis of this finding, by keeping the oxygen concentration in the gas phase to be at least 3 vol ppm, it is not necessary to reduce the oxygen concentration to the utmost limit close to 0 vol ppm, and it is thereby possible to suppress e.g. production cost. In the gas phase, the oxygen concentration is more preferably at least 5 vol ppm and less than 1,000 vol ppm, most preferably at least 6 vol ppm and at most 500 vol ppm at 25° C.

The oxygen concentration in the gas phase can be controlled in such a manner that tetrafluoropropene is pressurized to form liquid, and this liquid is injected into a closed container which is preliminarily evacuated of air to reduce the oxygen concentration to be less than 3,000 vol ppm at 25° C. When the liquid of tetrafluoropropene is injected into the container, a space in the container is quickly saturated with vapor from the liquid. Further, the oxygen concentration in the gas phase filled with saturated vapor of tetrafluoropropene as such becomes at least 3 vol ppm and less than 3,000 vol ppm (temperature: 25° C.).

Further, when the closed container is evacuated of air, non-condensable gas such as nitrogen is also removed together with oxygen, but the total content of the non-condensable gas is controlled so as not to exceed 1.5 vol % (15,000 vol ppm) at 25.0° C.

According to such a method for storing tetrafluoropropene of the present invention, it is possible to prevent reaction such as polymerization of tetrafluoropropene filled in a closed container in a gaseous-liquid state, and it is thereby possible to maintain a high purity and a high quality of tetrafluoropropene as e.g. a refrigerant. Further, since no polymerization product in a solid form is produced in a closed container, there is no fear of clogging of e.g. a valve or contamination of impurities into a cooling system. Further, it is possible to store tetrafluoropropene at a low cost.

Evaluation of the storing method of the present invention is carried out in such a manner that tetrafluoropropene in a gaseous-liquid state is injected into a closed container together with a prescribed amount of oxygen, they are entirely heated to a prescribed temperature and held for a prescribed time in a constant temperature state, and then a reaction product in a liquid phase of tetrafluoropropene is identified and analyzed. This evaluation corresponds to an acceleration test conducted by applying a heat load. A heating temperature may be set to a range of from −70 to 300° C. as a set temperature range of a constant temperature bath. Further, a heat treatment time may optionally be set. The reaction product may be identified and analyzed by e.g. methods described in Examples as mentioned below.

EXAMPLES

Now, the present invention will be described in detail with reference to Examples, but it should be understood that the present invention is by no means restricted thereto. Ex. 1 to 6 are Examples of the present invention, and Ex. 7 to 10 are Comparative Examples.

Ex. 1 to 10

Into a SUS316-made pressure resistant container (maximum working temperature: 300° C., maximum working pressure: 20 MPa) having an internal capacity of 200 cc, an incubation tube made of Pyrex (registered trademark) having its weight preliminary measured was inserted, the pressure resistant container was closed, and then the container was evacuated of air. Here, the incubation tube was inserted so as to confirm the presence or the absence of formation of a polymerization product in the pressure resistant container.

Then, a prescribed amount of oxygen was sealed in the above pressure resistant container, and then 100 g of liquefied tetrafluoropropene having a purity of 99.5% or higher was filled therein, so that the oxygen concentration in the gas phase would be a value shown in Table 1 at 25° C. Further, as tetrafluoropropene, HFO-1234yf was used.

Then, the pressure resistant container in which HFO-1234yf was filled together with a prescribed concentration of oxygen was installed in a hot air circulating constant temperature tank, and left to stand for 20 days in a constant temperature state of 60° C.

After expiration of 20 days, the pressure resistant container was taken out from the constant temperature tank, and HFO-1234yf was discharged therefrom. Further, the incubation tube was visually observed to confirm whether a solidified material was formed or not, and at the same time, the amount of the solidified material formed was measured to obtain a weight change before and after the test of the incubation tube. The results are shown in Table 1. In Table 1, ⊚ indicates "a case where no solidified material was present", ○ indicates "a case where a solidified material was somewhat formed, but there are practically no problems", and x indicates "a case where a solidified material was present", respectively.

Then, in each of Ex. 7 to 10 in which a solidified material was visually observed, the solidified material in the incubation tube was collected and dissolved in deuterated acetone to measure $^1$H-NMR, $^{13}$C-NMR and $^{19}$F-NMR spectra. The solidified material was identified by assignment of peaks in the NMR spectra measured, whereupon it was found to be a homopolymer of tetrafluoropropene. It is estimated that this homopolymer was formed by polymerization of HFO-1234yf.

TABLE 1

| | Oxygen concentration in gas phase (vol ppm) | Presence or absence of solidified product | Amount of solidified product formed (mg) |
|---|---|---|---|
| Ex. 1 | 6 | ⊚ | <3 |
| Ex. 2 | 100 | ⊚ | <3 |
| Ex. 3 | 200 | ⊚ | <3 |
| Ex. 4 | 500 | ⊚ | <3 |
| Ex. 5 | 1000 | ○ | 20 |
| Ex. 6 | 2000 | ○ | 100 |
| Ex. 7 | 5000 | X | 700 |
| Ex. 8 | 7000 | X | 1300 |
| Ex. 9 | 10000 | X | 2000 |
| Ex. 10 | 20000 | X | 4300 |

As shown in Table 1, in Ex. 1 to 6, no tetrafluoropropylene homopolymer as a solidified product which is practically problematic is observed in the liquid phase, especially in Ex. 1 to 4, the above solidified product is not observed, and therefore it is found that no polymerization reaction of HFO-1234yf takes place. On the other hand, in Ex. 7 to 10, formation of a homopolymer of tetrafluoropropene is observed. Accordingly, it is found that the method of the present invention is effective as a stable storing method by which no polymerization reaction occurs for a long period.

INDUSTRIAL APPLICABILITY

According to the storing method and the storing container of the present invention, tetrafluoropropene undergoes no reaction such as polymerization, and therefore tetrafluoropropene can be stored and transported while maintaining its high quality.

What is claimed is:
1. A closed container containing tetrafluoropropene in a gaseous-liquid state comprising a gas phase and a liquid phase, wherein an oxygen concentration in the gas phase is at least 3 vol ppm and less than 3,000 vol ppm at a temperature of 25° C.
2. The closed container according to claim 1, wherein the oxygen concentration in the gas phase is at least 5 vol ppm and less than 1,000 vol ppm at a temperature of 25° C.
3. The closed container according to claim 1, wherein the tetrafluoropropene is 2,3,3,3-tetrafluoropropene.

* * * * *